(12) United States Patent
Thorn et al.

(10) Patent No.: US 7,420,097 B2
(45) Date of Patent: Sep. 2, 2008

(54) SYNTHESIS OF 6-ARYL-6-ALKYL FULVENES, 6-ARYL-6-ALKENYL FULVENES, AND RELATED COMPOUNDS

(75) Inventors: Matthew G. Thorn, Bartlesville, OK (US); Michael D. Jensen, Bartlesville, OK (US); Joel L. Martin, Bartlesville, OK (US); Qing Yang, Bartlesville, OK (US); James L. Smith, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 535 days.

(21) Appl. No.: 10/877,021

(22) Filed: Jun. 25, 2004

(65) Prior Publication Data

US 2005/0288524 A1 Dec. 29, 2005

(51) Int. Cl.
*C07C 1/28* (2006.01)
*C07C 1/32* (2006.01)

(52) U.S. Cl. ...................................... 585/357; 585/359

(58) Field of Classification Search ................ 585/357, 585/359; 502/171, 152, 169
See application file for complete search history.

(56) References Cited

U.S. PATENT DOCUMENTS

| | | | |
|---|---|---|---|
| 3,381,017 | A | 4/1968 | Waugh |
| 4,611,024 | A | 9/1986 | Wolfe |
| 5,001,176 | A | 3/1991 | Nakazima |
| 5,015,679 | A | 5/1991 | Matumura |
| 5,179,063 | A | 1/1993 | Harris et al. |
| 5,744,666 | A | 4/1998 | Welch et al. |
| 6,025,512 | A | 2/2000 | Crowther et al. |
| 6,156,845 | A | 12/2000 | Saito et al. |
| 6,175,027 | B1 | 1/2001 | Sullivan et al. |
| 6,187,880 | B1 | 2/2001 | Welch et al. |
| 6,231,804 | B1 | 5/2001 | Yamauchi et al. |
| 6,291,382 | B1 | 9/2001 | Koppl et al. |
| 6,313,225 | B2 | 11/2001 | Saito et al. |
| 6,534,665 | B1 | 3/2003 | Nunez et al. |
| 2005/0080296 | A1 | 4/2005 | Park et al. |

OTHER PUBLICATIONS

Day, J. H.; The Fulvenes, Mar. 16, 1953, 167-189, Department of Chemistry, Ohio University, Athens, Ohio, USA.
Bergmann, E. D., The Fulvenes, Progress in Organic Chemistry. 1955, pp. 81-171, 3. Academic Press Inc., New York. USA.
Gilman, H.; Gorisch, R. D.; Reactions of Lithium with Some Aromatic Hydrocarbons in Tetrahydrofuran, Apr. 1958, 550-551, vol. 23, Chemistry Department of Iowa State College, Arnes, Iowa, USA.
Yates, P., Fulvenes, Advances in Alicyclic Chemistry, 1968, pp. 60-184, vol. 2, Academic Press, New York, USA.
Stone, K. J.; Little, R. D.; An Exceptionally Simple and Efficient Method for the Preparation of a Wide Variety of Fulvenes, The Journal of Organic Chemistry, Jun. 1, 1984, 1849-1853, vol. 49-11, American Chemical Society.
Li, J. H.; Liu, J. T.; Jiao, L. J.; Zhang, X. Q.; Ma, Y. D.; Zhang, N.; Reaction of Substituted Cyclopentadienyl-Magnesium-Chloride with Carbonyl Compound (I): Research in Chinese Universities, 1992, 370-376; vol. 8-4, Shandong Province. China.
Xiao, Ya-Ping, et al., "One Step Synthesis of Dicyclopentadienylmagnesium and its Reaction . . . " Youji Huaxue/ Organic Chemistry, vol. 16, No. 5 (1996) pp. 450-452.
Fierro, R., et al. "Synthesis and Characterization of New One-Carbon-Britdged . . . " J of Organo. Chem., Elsevier-Sequola SA Lausanne, CH, vol. 485, No. 1 (1995) pp. 11-17.
Alt, H G. et al., "C1-Bridged Fluorenylidene Cyctopentadienylidene Complexes . . . ", J of Organo. Chem. Elsevier-Sequoia SA Lausanne, CH, vol. 568, No. 1-2 (1998), pp. 87-112.
Search Report for International Application No. PCT/US2005/ 0022746 dated Dec. 19, 2005.
Youji Huaxue, Organic Chemistry, 1996, vol. 16, pp. 450-452, Research Bulletin.

*Primary Examiner*—Thuan Dinh Dang
(74) *Attorney, Agent, or Firm*—Fletcher Yoder

(57) ABSTRACT

The present invention provides a method of making fulvenes, particularly 6-aryl-6-alkylfulvenes, 6-aryl-6-alkenylfulvenes, and related compounds, by combining alkyl- or alkenyl-arylketones with magnesium cyclopentadienyl reagents in nonprotic, including ethereal, solvents. The use of these compounds in preparing bis(cyclopentadienyl)methanes and related compounds, and ansa-metallocenes, is disclosed.

34 Claims, No Drawings

SYNTHESIS OF 6-ARYL-6-ALKYL FULVENES, 6-ARYL-6-ALKENYL FULVENES, AND RELATED COMPOUNDS

TECHNICAL FIELD OF THE INVENTION

This invention relates to the field of organic synthesis, including synthetic methods for fulvenes, bis(cyclopentadienyl)methanes and related compounds, and ansa-metallocenes.

BACKGROUND OF THE INVENTION

Metallocenes constitute useful compounds for olefin polymerizations when combined with a cocatalyst such as aluminoxane. It is generally accepted that the properties of the polymers formed using such a combination are determined in large part by the structural nature of the metallocene, including its steric and electronic features. Therefore, there is a need to develop new methods to prepare metallocenes that allow an assortment of diverse substituents to be incorporated into the metallocene structure.

Fulvenes, having the general formula $C_4R''_4C{=}CRR'$ and the structure

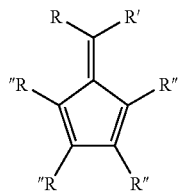

are often-useful precursors to metallocenes and can provide a means for integrating a range of substituents into the metallocene structure. One aspect of this utility can be seen from the reaction of fulvenes with cyclopentadienyl-, indenyl-, and fluorenyl-lithium reagents as illustrated in Scheme 1, because the resulting products can be used as ligand precursors to form bridged or ansa-metallocenes. Ansa-metallocene catalysts are useful in olefin polymerizations and copolymerizations, in part because of impact the tailored ligand set can have on the properties of the resulting polymer.

Scheme 1

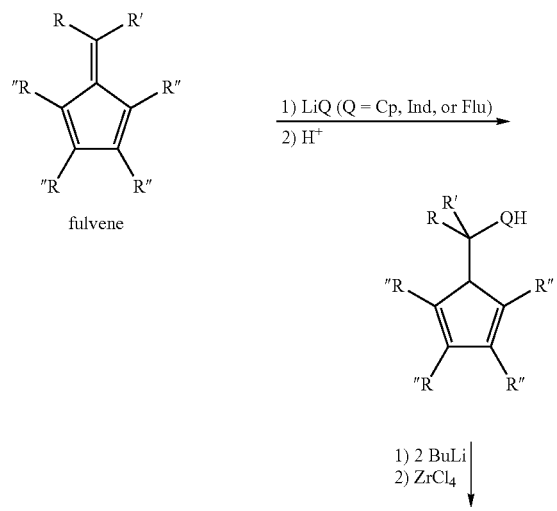

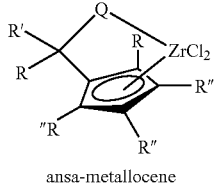

ansa-metallocene

Therefore, it is of interest to develop new methods to prepare fulvenes that may provide these ligands in higher yields or with greater selectively. It is also of interest to develop new methods to prepare ansa-metallocenes based on new fulvene synthetic methods.

SUMMARY OF THE INVENTION

This invention encompasses methods for the selective synthesis of 6-aryl-6-alkyl fulvenes, 6-aryl-6-alkenyl fulvenes, and similar compounds, which constitute useful intermediates in preparing metallocene complexes that can be subsequently used as catalyst components in olefin polymerizations. In one aspect, the methods of this invention afford higher chemical selectivity and higher yields of the desired product than were heretofore available. Traditional methods to prepare 6-aryl-6-alkyl fulvenes and 6-aryl-6-alkenyl fulvenes include the reaction of metal alkoxides with cyclopentadienes and ketones or aldehydes in an alcoholic (protic) solvent. While this method can afford some of the desired product, a mixture of isomers or tautomers in varying concentrations is typically generated, thereby rendering isolation, purification, and subsequent use of the desired isomer tedious and difficult.

In one aspect, this present invention provides a method of selectively preparing 6-aryl-6-alkyl fulvenes, 6-aryl-6-alkenyl fulvenes, and similar compounds, having the general formula $C_4R^3{}_4C{=}CR^1CH_2R^2$ and the structure

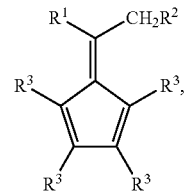

or an isomer thereof;

wherein $R^1$ is an aryl or substituted aryl group; $R^2$ is a hydrocarbyl or substituted hydrocarbyl group or hydrogen; and $R^3$, in each instance, is independently selected from a hydrocarbyl or substituted hydrocarbyl group; by reacting aryl-alkylketones or aryl-alkenylketones with magnesium-cyclopentadienyl reagents in aprotic solvents. In this aspect, ethereal solvents were typically employed. This method afforded the desired fulvene compound either exclusively or in large excess over the undesired isomer, thereby greatly simplifying its isolation and purification. In one aspect, a Grignard cyclopentadienyl reagent was typically used in the synthesis, which afforded a higher yield of the desired product, in addition to providing a highly selective reaction.

In another aspect, the present invention provides a method of making bis(cyclopentadienyl)methane compounds, and various analogs such as (cyclopentadienyl)(indenyl)methane and (cyclopentadienyl)(fluorenyl)methane compounds, hav ing the general formula $C_4R^3{}_4CHCR^1(CH_2R^2)(QH)$ and the structure:

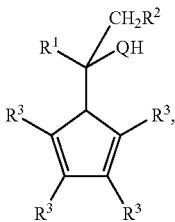

wherein Q is a cyclopentadienyl, an indenyl, a fluorenyl, or a substituted analog thereof. In a further aspect, this invention provides ansa-metallocene compounds, including ansa-metallocenes containing a pendant unsaturated moiety attached to the bridge.

In yet another aspect, this invention provides a method of making a compound having the formula $C_4R^3{}_4C=CR^1CH_2R^2$ and the structure:

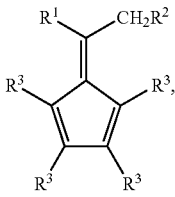

or an isomer thereof,
comprising contacting in a nonprotic solvent:
  a) a ketone of the formula $O=CR^1CH_2R^2$; and
  b) a cyclopentadienyl compound comprising $Mg(C_5R^3{}_4H)X$, $Mg(C_5R^3{}_4H)_2$, or a combination thereof; followed by
  c) a proton source;
wherein:
  $R^1$ is an aryl or substituted aryl group having up to about 20 carbon atoms;
  $R^2$ is a hydrocarbyl or substituted hydrocarbyl group having from 1 to about 20 carbon atoms, or hydrogen;
  $R^3$, in each instance, is independently selected from a hydrocarbyl or substituted hydrocarbyl group having from 1 to about 20 carbon atoms, or hydrogen; and
  X is Cl, Br, or I.

In still another aspect, the present invention provides a method of making a compound having the formula $C_4R^3{}_4CHCR^1(CH_2R^2)(QH)$ and the structure:

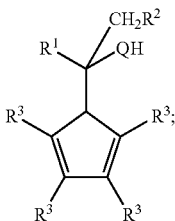

comprising:
  1) contacting in a nonprotic solvent:
  a) a ketone of the formula $O=CR^1CH_2R^2$; and
  b) a cyclopentadienyl compound comprising $Mg(C_5R^3{}_4H)X$, $Mg(C_5R^3{}_4H)_2$, or a combination thereof; followed by
  c) a proton source;

to form a compound having the formula $C_4R^3{}_4C=CR^1CH_2R^2$ and the structure:

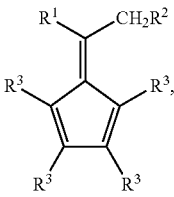

or an isomer thereof,
wherein:
  $R^1$ is an aryl or substituted aryl group having up to about 20 carbon atoms;
  $R^2$ is a hydrocarbyl or substituted hydrocarbyl group having from 1 to about 20 carbon atoms, or hydrogen;
  $R^3$, in each instance, is independently selected from a hydrocarbyl or substituted hydrocarbyl group having from 1 to about 20 carbon atoms, or hydrogen; and
  X is Cl, Br, or I; and
  2) contacting
  a) $C_4R^3{}_4C=CR^1CH_2R^2$ with MQ, wherein M is Li, Na, K, MgX, or $Mg_{0.5}$, wherein X is Cl, Br, or I, and wherein Q is a cyclopentadienyl, an indenyl, a fluorenyl, or a substituted analog thereof; followed by
  b) a proton source, to form $C_4R^3{}_4CHCR^1(CH_2R^2)(QH)$.

Yet another aspect of this invention is a method of making an ansa-metallocene having the formula $(\eta^5\text{-}C_5R^3{}_4)CR^1(CH_2R^2)(\eta^5\text{-}Q)M^1X_2$, wherein $M^1$ is titanium, zirconium, or hafnium, and X is a halide, comprising:
  1) contacting in a nonprotic solvent:
  a) a ketone of the formula $O=CR^1CH_2R^2$; and
  b) a cyclopentadienyl compound comprising $Mg(C_5R^3{}_4H)X$, $Mg(C_5R^3{}_4H)_2$, or a combination thereof; followed by
  c) a proton source;
to form a compound having the formula $C_4R^3{}_4C=CR^1CH_2R^2$ and the structure:

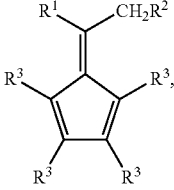

or an isomer thereof,
wherein:
  $R^1$ is an aryl or substituted aryl group having up to about 20 carbon atoms;
  $R^2$ is a hydrocarbyl or substituted hydrocarbyl group having from 1 to about 20 carbon atoms, or hydrogen;
  $R^3$, in each instance, is independently selected from a hydrocarbyl or substituted hydrocarbyl group having from 1 to about 20 carbon atoms, or hydrogen; and
  X is Cl, Br, or I;
  2) contacting
  a) $C_4R^3{}_4C=CR^1CH_2R^2$ with MQ, wherein M is Li, Na, K, MgX, or $Mg_{0.5}$, wherein X is Cl, Br, or I, and wherein Q is a cyclopentadienyl, an indenyl, a fluorenyl, or a substituted analog thereof; followed by
  b) a proton source, to form $C_4R^3{}_4CHCR^1(CH_2R^2)(QH)$ having the structure:

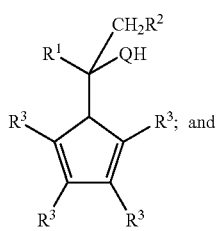

3) contacting $C_4R^3{}_4CHCR^1(CH_2R^2)(QH)$ with about 2 equivalents of a base and a compound of the formula $M^1X_4$.

These and other features, aspects, embodiments, and advantages of the present invention will become apparent after a review of the following detailed description of the disclosed features.

The following patent applications, filed contemporaneously with the present application, are incorporated by reference herein in their entireties: U.S. patent application Ser. No. 10/877,039 U.S. patent application Ser. No. 10/876,891; U.S. patent application Ser. No. 10/876,930; and U.S. patent application Ser. No.10/876,948.

DETAILED DESCRIPTION OF THE INVENTION

The present invention provides a method of making fulvenes, particularly 6-aryl-6-alkylfulvenes, 6-aryl-6-alkenyl-fulvenes, and similar compounds, by combining alkyl- or alkenyl-arylketones with magnesium-cyclopentadienyl reagents in nonprotic solvents, including ethereal solvents. This invention also provides for the use of these fulvenes in preparing bis(cyclopentadienyl)methane compounds and related chemicals such as (cyclopentadienyl)(indenyl)methane and (cyclopentadienyl)(fluorenyl)methane compounds, as well as ansa-metallocenes. This invention also provides a process of combining an α-aromatic substituted carbonyl compound of the formula $O=CR^1CH_2R^2$, wherein $R^1$ is an aryl or substituted aryl group and $R^2$ is a hydrocarbyl or substituted hydrocarbyl group, or hydrogen, with a magnesium cyclopentadienyl reagent in nonprotic solvents to form fulvenes. Generally, and in another aspect, this invention affords improved yields and enhanced selectivity in fulvene syntheses.

Preparation of Fulvene Compounds

Fulvenes themselves have been known since the early 1900s. See, for example: *Chem. Rev.* 1953, 53(2), 167; *Chem. Rev.* 1967, 68(1), 41; *Progr. Org. Chem.* 1955, 3, 41; *Adv. Alicyclic Chem.* 1968, 2, 59; and *J. Org. Chem.*, 1984, 49, 1849; each of which is incorporated herein by reference in its entirety. These publications, and the references cited therein, describe many of the known methods for formation of fulvenes as well as their various physical properties. Two common methods for preparing fulvenes are as follows: a) the reaction of cyclopentadiene with sodium or potassium alkoxides in the presence of ketones or aldehydes in an alcoholic solvent; and b) the reaction of cyclopentadiene with ketones or aldehydes in the presence of pyrollidine, also in an alcoholic solvent (see: *J. Org. Chem.*, 1984, 49, 1849). These methods are illustrated herein as equations 1 and 2, respectively, where the results of their application to a ketone precursor having the formula $O=CR^1CH_2R^2$, wherein $R^1$ is an aryl (or substituted aryl) group, are demonstrated.

(1)

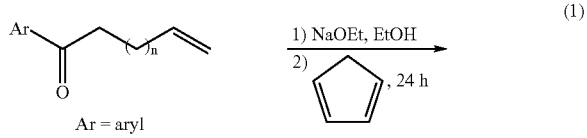

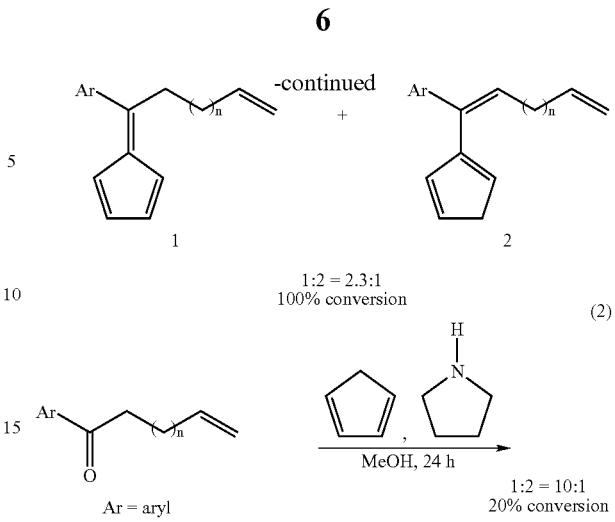

As equations 1 and 2 indicate, issues of selectivity and yield arise when the ketone comprises an aryl substituent ($R^1$ in the structure), and a hydrocarbyl substituent with at least one α-hydrogen adjacent to the carbonyl functionality. In one aspect, for example, when $R^1$ of the formula $O=CR^1CH_2R^2$ is an aryl or substituted aryl group, and when $R^2$ of this formula is an aliphatic or substituted aliphatic group or hydrogen, employing the method illustrated in equation 1 leads to a mixture of isomeric fulvene compounds 1 and 2, that are difficult to separate by conventional means. Employing the method illustrated in equation 2 for a ketone of the formula $O=CR^1CH_2R^2$ described herein affords a reaction that is sufficiently slow and unselective to be undesirable. While not intending to be bound by theory, it is believed that the aryl substituent $R^1$ imparts a comparatively higher reactivity to the α-hydrogen adjacent to the carbonyl group, which likely leads to the poor selectivity observed.

In one aspect, for example, the synthetic methods of the present invention are illustrated herein, though not exhaustively, by the general equations shown in equations 3 and 4. As indicated in these equations, a gas chromatographic analysis of the reaction mixture indicated at least about an 80% conversion of the starting ketone to the desired fulvene product was typically obtained, with 100% selectivity, that is, 100% of the fulvene formed constituted the desired isomer.

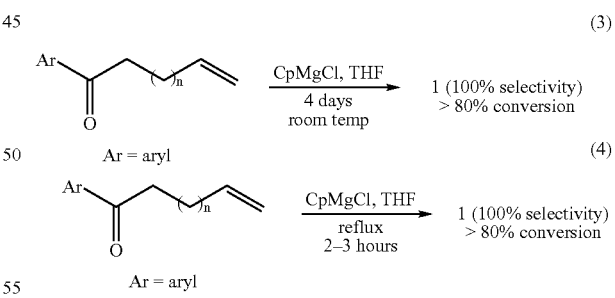

In another aspect, this invention provides a synthetic approach to 6-aryl-6-alkylfulvenes and 6-aryl-6-alkenylfulvenes by reacting cyclopentadiene or a cyclopentadiene analog with a base such as an alkylmagnesium halide in an aprotic (also termed nonprotic) solvent as a reaction medium. Generally, the aprotic solvent used can be an ethereal solvent such as diethyl ether, dibutyl ether, methyl t-butyl ether, diphenyl ether, tetrahydrofuran, 1,2-dimethoxyethane, and the like, or combinations thereof. Reacting the thus-formed cyclopentadienyl anion with an aryl-alkenylketone or aryl-alkylketone in an aprotic solvent as a reaction medium (such as diethyl ether, dibutyl ether, tetrahydrofuran, 1,2-dimethoxyethane, and the like), and refluxing the solvent as needed, followed by hydrolytic workup or neutralization using a weak acid (such as dilute hydrochloric acid and the like) affords the desired product.

In another aspect, the cyclopentadiene or a cyclopentadiene analog can also be reacted with a dialkylmagnesium compound in an aprotic solvent as a reaction medium. As disclosed herein for the Grignard reagents, the aprotic solvents used in this case can also be ethereal solvent such as diethyl ether, dibutyl ether, methyl t-butyl ether, diphenyl ether, tetrahydrofuran, and the like.

While not intending to be bound by theory, it is thought that the use of an ethereal solvent such as dimethyl ether, diethyl ether, diisopropyl ether, di-n-propyl ether, di-n-butyl ether, methyl t-butyl ether, diphenyl ether, THF, 1,2-dimethoxyethane, or any combination thereof, may assist the reaction of the cyclopentadienyl anion with an aryl-alkenylketone or aryl-alkylketone. It is believed that the acidity of the protons next to a ketone-functional group is due to the aryl substituent, and using the aprotic, ethereal solvents instead of a protic solvent such as an alcohol provides the high selectivity and high yields observed.

Thus, in one aspect, the present invention provides a method of making a compound having the formula $C_4R^3_4C=CR^1CH_2R^2$ and the structure:

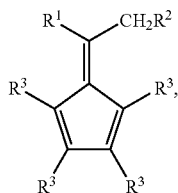

or an isomer thereof, comprising contacting in a nonprotic solvent:
a) a ketone of the formula $O=CR^1CH_2R^2$; and
b) a cyclopentadienyl compound comprising $Mg(C_5R^3_4H)X$, $Mg(C_5R^3_4H)_2$, or a combination thereof; followed by
c) a proton source;

wherein:
$R^1$ is an aryl or substituted aryl group having up to about 20 carbon atoms;
$R^2$ is a hydrocarbyl or substituted hydrocarbyl group having from 1 to about 20 carbon atoms, or hydrogen;
$R^3$, in each instance, is independently selected from a hydrocarbyl or substituted hydrocarbyl group having from 1 to about 20 carbon atoms, or hydrogen; and
X is Cl, Br, or I.

The proton source can be any compound or combination of compounds that can serve as a source of protons to the formal anion formed upon reacting the ketone with the cyclopentadienyl reagent. In this aspect, for example, the proton source can be water, an acid including an aqueous acid, ammonium salts including aqueous solutions of ammonium salts, and the like. For example, aqueous HCl can be used in this reaction.

All of the $R^3$ substituents on the fulvene structure shown here

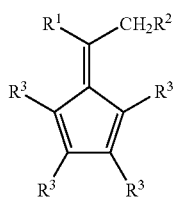

are not required to be the same, which is indicated by specifying that $R^3$, in each instance, is independently selected from a hydrocarbyl or substituted hydrocarbyl group having from 1 to about 20 carbon atoms, or hydrogen. Thus, $R^3$ can be selected such that the fulvene is substituted with 4 hydrogens and no non-hydrogen substituents, with 3 hydrogens and a single non-hydrogen substituent, with 2 hydrogens and 2 non-hydrogen substituents, with 1 hydrogen and 3 non-hydrogen substituents, or with no hydrogens and 4 non-hydrogen substituents.

In one aspect, the possible substitution patterns on the fulvene compound depicted in the generic structure herein lead to the possibility of isomers. For example, when three $R^3$ moieties are independently selected to be hydrogen, and the fourth $R^3$ moiety is independently selected to be methyl, the following isomers are possible.

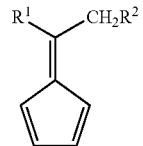

A

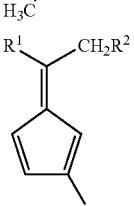

B

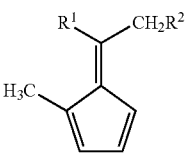

C

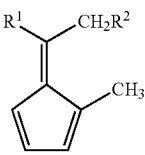

D

While not intending to be bound by theory, it is believed that because the fulvene is prepared by the nucleophilic reaction of a cyclopentadienyl reagent with a ketone, isomers A and B are likely to predominate. The addition of a cyclopentadienyl, indenyl, or fluorenyl anion to a mixture of these isomers renders A and B equivalent and also renders C and D equivalent. However, when the metal complex of the ligand is formed, the complexes derived from A and B are enantiomeric, and the complexes derived from C and D are enantiomeric. Accordingly, when all of the $R^3$ substituents in the fulvene formula $C_4R^3_4C=CR^1CH_2R^2$ are not the same, it is intended that the general structure

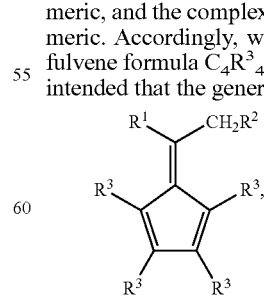

disclosed herein refers to any isomers that arise from the possible substitution patterns in this structure.

In another aspect, $R^1$ can be phenyl, naphthyl, or a substituted analog thereof having up to about 20 carbon atoms. Thus, for example, $R^1$ can be phenyl or naphthyl. Also in this aspect, $R^2$ can be alkyl, aryl, alkenyl, or a substituted analog thereof, having from 1 to about 20 carbon atoms, or hydrogen. Thus, for example, $R^2$ can be alkyl or alkenyl having from 3 to about 10 carbon atoms. In still another aspect of this invention, $CH_2R^2$ can be:

$CH_2CH_3$;
$CH_2CH_2CH_3$;
$CH_2CH_2CH_2CH_3$;
$CH_2CH_2CH_2CH_2CH_3$;
$CH_2CH_2CH_2CH_2CH_2CH_3$;
$CH_2CH_2CH_2CH_2CH_2CH_2CH_3$;
$CH_2CH_2CH_2CH_2CH_2CH_2CH_2CH_3$;
$CH_2CH_2CH_2CH_2CH_2CH_2CH_2CH_2CH_3$;
$CH_2CH_2CH_2CH_2CH_2CH_2CH_2CH_2CH_2CH_3$;
$CH_2CH=CH_2$;
$CH_2CH_2CH=CH_2$;
$CH_2CH_2CH_2CH=CH_2$;
$CH_2CH_2CH_2CH_2CH=CH_2$;
$CH_2CH_2CH_2CH_2CH_2CH=CH_2$;
$CH_2CH_2CH_2CH_2CH_2CH_2CH=CH_2$;
$CH_2CH_2CH_2CH_2CH_2CH_2CH_2CH=CH_2$;
$CH_2CH_2CH_2CH_2CH_2CH_2CH_2CH_2CH=CH_2$;
$CH_2CH_2C(CH_3)=CH_2$;
$CH_2CH_2CH=C(CH_3)_2$;
$CH_2C_6H_5$;
$CH_2C_6H_4Me$;
$CH_2C_6H_3Me_2$;
$CH_2C_6H_2Me_3$;
$CH_2C_6H_4(C_6H_{11})$;
$CH_2C_6H_4(C_6H_5)$; or $CH_2C_6H_4(C_4H_9)$;

including isomers thereof and substituted analogs thereof, having up to about 20 carbon atoms. In yet another aspect, $R^3$, in each instance, can be independently selected from alkyl having from 1 to about 4 carbon atoms; or hydrogen. For example, $R^3$, in each instance, can be hydrogen.

Yet another aspect of this invention is a method of making a compound having the formula $C_4R^3{}_4C=CR^1CH_2R^2$ and the structure:

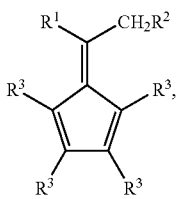

comprising contacting in a nonprotic solvent:
a) a ketone of the formula $O=CR^1CH_2R^2$; and
b) a cyclopentadienyl compound comprising $Mg(C_5R^3{}_4H)X$, $Mg(C_5R^3{}_4H)_2$, or a combination thereof; followed by
c) a proton source;

wherein the ketone can be:
$O=C(C_6H_5)CH_2CH=CH_2$;
$O=C(C_6H_5)CH_2CH_2CH=CH_2$;
$O=C(C_6H_5)CH_2CH_2CH_2CH=CH_2$;
$O=C(C_6H_5)CH_2CH_2CH_2CH_2CH=CH_2$;
$O=C(C_6H_5)CH_2CH_2CH_2CH_2CH_2CH=CH_2$;
$O=C(C_6H_4CH_3)CH_2CH=CH_2$;
$O=C(C_6H_4CH_3)CH_2CH_2CH=CH_2$;
$O=C(C_6H_4CH_3)CH_2CH_2CH_2CH=CH_2$;
$O=C(C_6H_4CH_3)CH_2CH_2CH_2CH_2CH=CH_2$;
$O=C(C_6H_4CH_3)CH_2CH_2CH_2CH_2CH_2CH=CH_2$;
$O=C[C_6H_3(CH_3)_2]CH_2CH=CH_2$;
$O=C[C_6H_3(CH_3)_2]CH_2CH_2CH=CH_2$;
$O=C[C_6H_3(CH_3)_2]CH_2CH_2CH_2CH=CH_2$;
$O=C[C_6H_3(CH_3)_2]CH_2CH_2CH_2CH_2CH=CH_2$;
$O=C[C_6H_3(CH_3)_2]CH_2CH_2CH_2CH_2CH_2CH=CH_2$;
$O=C[C_6H_2(CH_3)_3]CH_2CH=CH_2$;
$O=C[C_6H_2(CH_3)_3]CH_2CH_2CH=CH_2$;
$O=C[C_6H_2(CH_3)_3]CH_2CH_2CH_2CH=CH_2$;
$O=C[C_6H_2(CH_3)_3]CH_2CH_2CH_2CH_2CH=CH_2$;
$O=C[C_6H_2(CH_3)_3]CH_2CH_2CH_2CH_2CH_2CH=CH_2$;
$O=C[C_6H_4(C_6H_{11})]CH_2CH=CH_2$;
$O=C[C_6H_4(C_6H_{11})]CH_2CH_2CH=CH_2$;
$O=C[C_6H_4(C_6H_{11})]CH_2CH_2CH_2CH=CH_2$;
$O=C[C_6H_4(C_6H_{11})]CH_2CH_2CH_2CH_2CH=CH_2$;
$O=C[C_6H_4(C_6H_{11})]CH_2CH_2CH_2CH_2CH_2CH=CH_2$;
$O=C[CH_2C_6H_4(C_6H_5)]CH_2CH=CH_2$;
$O=C[CH_2C_6H_4(C_6H_5)]CH_2CH_2CH=CH_2$;
$O=C[CH_2C_6H_4(C_6H_5)]CH_2CH_2CH_2CH=CH_2$;
$O=C[CH_2C_6H_4(C_6H_5)]CH_2CH_2CH_2CH_2CH=CH_2$;
$O=C[CH_2C_6H_4(C_6H_5)]CH_2CH_2CH_2CH_2CH_2CH=CH_2$;
$O=C[CH_2C_6H_4(C_4H_9)]CH_2CH=CH_2$;
$O=C[CH_2C_6H_4(C_4H_9)]CH_2CH_2CH=CH_2$;
$O=C[CH_2C_6H_4(C_4H_9)]CH_2CH_2CH_2CH=CH_2$;
$O=C[CH_2C_6H_4(C_4H_9)]CH_2CH_2CH_2CH_2CH=CH_2$;
$O=C[CH_2C_6H_4(C_4H_9)]CH_2CH_2CH_2CH_2CH_2CH=CH_2$;
$O=C(naphthyl)CH_2CH=CH_2$;
$O=C(naphthyl)CH_2CH_2CH=CH_2$;
$O=C(naphthyl)CH_2CH_2CH_2CH=CH_2$;
$O=C(naphthyl)CH_2CH_2CH_2CH_2CH=CH_2$;
$O=C(naphthyl)CH_2CH_2CH_2CH_2CH_2CH=CH_2$; or any isomer thereof, or any analog thereof wherein the alkenyl group is saturated. Still another aspect of this invention is a method of making a compound having the formula $C_4R^3{}_4C=CR^1CH_2R^2$ and the structure:

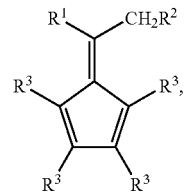

comprising contacting in a nonprotic solvent:
a) a ketone of the formula $O=CR^1CH_2R^2$; and
b) a cyclopentadienyl compound comprising $Mg(C_5R^3{}_4H)X$, $Mg(C_5R^3{}_4H)_2$, or a combination thereof; followed by
c) a proton source;

wherein the ketone can be:
$O=C(C_6H_5\text{-p-alkyl})CH_2CH_2CH=CH_2$,
$O=C(C_6H_5\text{-p-alkyl})CH_2CH_2CH_2CH=CH_2$,
$O=C(C_6H_5\text{-p-cycloalkyl})CH_2CH_2CH=CH_2$, or
$O=C(C_6H_5\text{-p-cycloalkyl})CH_2CH_2CH_2CH=CH_2$;

wherein p-alkyl and p-cycloalkyl have up to about 12 carbon atoms.

In a further aspect of this invention, a method of making a compound having the formula $C_4R^3{}_4C=CR^1CH_2R^2$ and the structure:

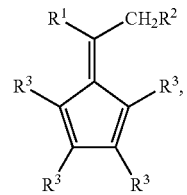

is disclosed,
comprising contacting in a nonprotic solvent:
a) a ketone of the formula $O=CR^1CH_2R^2$; and
b) a cyclopentadienyl compound comprising $Mg(C_5R^3{}_4H)X$, $Mg(C_5R^3{}_4H)_2$, or a combination thereof; followed by
c) a proton source;

wherein the cyclopentadienyl compound can comprise $Mg(C_5H_5)X$, wherein X is Cl, Br, or a combination thereof. Thus, for example, the cyclopentadienyl compound can comprise $Mg(C_5H_5)Cl$.

In a further aspect, the cyclopentadienyl compound can comprise $Mg(C_5H_5)X$ wherein X is Cl or Br, and the molar ratio of $Mg(C_5H_5)X$ to ketone can be greater than about 1. In another aspect, the molar ratio of $Mg(C_5H_5)X$ to ketone can be greater than about 1.2, or the molar ratio of $Mg(C_5H_5)X$ to ketone can be greater than about 1.5.

In yet another aspect, this invention provides a method of making a compound having the formula $C_4R^3{}_4C=CR^1CH_2R^2$ and the structure:

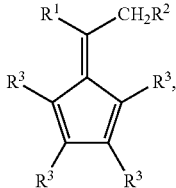

comprising contacting in a nonprotic solvent:
 a) a ketone of the formula $O=CR^1CH_2R^2$; and
 b) a cyclopentadienyl compound comprising $Mg(C_5R^3{}_4H)X$, $Mg(C_5R^3{}_4H)_2$, or a combination thereof; followed by
 c) a proton source;

wherein the nonprotic solvent is an ether having from 2 to about 20 carbon atoms, THF, a substituted analog thereof, or any combination thereof. Thus, the nonprotic solvent can comprise THF. In another aspect, for example, the nonprotic solvent can be dimethyl ether, diethyl ether, diisopropyl ether, di-n-propyl ether, di-n-butyl ether, methyl t-butyl ether, diphenyl ether, THF, 1,2-dimethyoxyethane, or any combination thereof. In one aspect, when the solvent comprises dimethyl ether, one method of performing this reaction is under pressure, so that the dimethyl ether may be refluxed at a higher temperature. This pressure method can also be applied to other solvents as well, such as diethyl ether.

Yet another aspect of this invention is a method of making a compound having the formula $C_4R^3{}_4C=CR^1CH_2R^2$ and the structure:

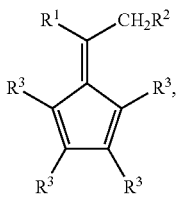

comprising contacting in a nonprotic solvent:
 a) a ketone of the formula $O=CR^1CH_2R^2$; and
 b) a cyclopentadienyl compound comprising $Mg(C_5R^3{}_4H)X$, $Mg(C_5R^3{}_4H)_2$, or a combination thereof; followed by
 c) a proton source;

wherein the nonprotic solvent comprises THF, and contacting can occur at a temperature greater than about 40° C. for at least about 10 hours. In this aspect, when the nonprotic solvent comprises THF, the contacting can occur at a temperature greater than about 50° C. for a time from about 5 to about 10 hours. Further, when the nonprotic solvent comprises THF, the contacting can occur at a temperature greater than about 65° C. for a time from about 1 to about 2 hours. In this aspect, when the nonprotic solvent comprises an ether with a boiling point greater than about 40° C., the contacting can occur at a temperature greater than about 40° C. for at least about 5 hours. Also in this aspect, for example, when contacting occurs at a temperature greater than about 40° C. for at least about 5 hours, the pressure can be selected such that the boiling point of the nonprotic solvent is about equal to or greater than the contacting temperature.

Possible Fulvene Substituents

In one aspect of this invention, any substituent on the substituted aryl group of $R^1$, any substituent on the substituted hydrocarbyl group of $R^2$, and any substituent on the substituted hydrocarbyl group of $R^3$ can be independently selected from a number of chemical moieties including, but not limited to, an aliphatic group, an aromatic group, a cyclic group, a combination of aliphatic and cyclic groups, an oxygen group, a sulfur group, a nitrogen group, a phosphorus group, an arsenic group, a carbon group, a silicon group, a germanium group, a tin group, a lead group, a boron group, an aluminum group, an inorganic group, an organometallic group, or a substituted derivative thereof, any one of which having from 1 to about 20 carbon atoms; a halide; or hydrogen, as long as these groups do not terminate the synthetic method for fulvene synthesis. Further, this description can include substituted, unsubstituted, branched, linear, or heteroatom-substituted analogs of these moieties.

This listing of possible substituents includes substituents that may be characterized in more than one of these categories such as benzyl. This list also includes hydrogen, therefore the notion of a substituted indenyl and substituted fluorenyl includes partially saturated indenyls and fluorenyls including, but not limited to, tetrahydroindenyls, tetrahydrofluorenyls, and octahydrofluorenyls.

Examples of each of these substituent groups include, but are not limited to, the following groups. In each example presented below, unless otherwise specified, R is independently selected from: an aliphatic group; an aromatic group; a cyclic group; any combination thereof; any substituted derivative thereof, including but not limited to, a halide-, an alkoxide-, or an amide-substituted derivative thereof; any one of which has from 1 to about 20 carbon atoms; or hydrogen. Also included in these groups are any unsubstituted, branched, or linear analogs thereof.

Examples of aliphatic groups, in each instance, include, but are not limited to, an alkyl group, a cycloalkyl group, an alkenyl group, a cycloalkenyl group, an alkynyl group, an alkadienyl group, a cyclic group, and the like, and includes all substituted, unsubstituted, branched, and linear analogs or derivatives thereof, in each instance having from one to about 20 carbon atoms. Thus, aliphatic groups include, but are not limited to, hydrocarbyls such as paraffins and alkenyls. For example, aliphatic groups as used herein include methyl, ethyl, propyl, n-butyl, tert-butyl, sec-butyl, isobutyl, amyl, isoamyl, hexyl, cyclohexyl, heptyl, octyl, nonyl, decyl, dodecyl, 2-ethylhexyl, pentenyl, butenyl, and the like.

Examples of aromatic groups, in each instance, include, but are not limited to, phenyl, biphenyl, naphthyl, anthracenyl, and the like, including substituted derivatives thereof, in each instance having from 6 to about 25 carbons. Substituted derivatives of aromatic compounds include, but are not limited to, tolyl, xylyl, mesityl, and the like, including any heteroatom substituted derivative thereof.

Examples of cyclic groups, in each instance, include, but are not limited to, cycloparaffins, cycloolefins, cycloacetylenes, arenes such as phenyl, bicyclic groups and the like, including substituted derivatives thereof, in each instance having from about 3 to about 20 carbon atoms. Thus heteroatom-substituted cyclic groups such as furanyl are included herein. The saturation state of the cyclic group can be any saturation state that does not preclude the synthetic methods as disclosed herein from any measure of effectiveness.

Accordingly, the cyclic groups can be saturated or be characterized by any extent of unsaturation.

In each instance, aliphatic and cyclic groups are groups comprising an aliphatic portion and a cyclic portion, examples of which include, but are not limited to, groups such as: $-(CH_2)_m C_6 H_q R_{5-q}$ wherein m is an integer from 1 to about 10, q is an integer from 1 to 5, inclusive; $-(CH_2)_m C_6 H_q R_{11-q}$ wherein m is an integer from 1 to about 10, q is an integer from 1 to 11, inclusive; and $-(CH_2)_m C_5 H_q R_{9-q}$ wherein m is an integer from 1 to about 10, q is an integer from 1 to 9, inclusive. In each instance and as defined above, R is independently selected from: an aliphatic group; an aromatic group; a cyclic group; any combination thereof; any substituted derivative thereof, including but not limited to, a halide-, an alkoxide-, or an amide-substituted derivative thereof; any one of which has from 1 to about 20 carbon atoms; or hydrogen. In one aspect, aliphatic and cyclic groups include, but are not limited to: $-CH_2C_6H_5$; $-CH_2C_6H_4F$; $-CH_2C_6H_4Cl$; $-CH_2C_6H_4Br$; $-CH_2C_6H_4I$; $-CH_2C_6H_4OMe$; $-CH_2C_6H_4OEt$; $-CH_2C_6H_4NH_2$; $-CH_2C_6H_4NMe_2$; $-CH_2C_6H_4NEt_2$; $-CH_2CH_2C_6H_5$; $-CH_2CH_2C_6H_4F$; $-CH_2CH_2C_6H_4Cl$; $-CH_2CH_2C_6H_4Br$; $-CH_2CH_2C_6H_4I$; $-CH_2CH_2C_6H_4OMe$; $-CH_2CH_2C_6H_4OEt$; $-CH_2CH_2C_6H_4NH_2$; $-CH_2CH_2C_6H_4NMe_2$; $-CH_2CH_2C_6H_4NEt_2$; any regioisomer thereof, and any substituted derivative thereof.

Examples of halides, in each instance, include fluoride, chloride, bromide, and iodide.

In each instance, oxygen groups are oxygen-containing groups, examples of which include, but are not limited to, alkoxy or aryloxy groups (—OR), $-OSiR_3$, $-OPR_2$, $-OAlR_2$, and the like, including substituted derivatives thereof, wherein R in each instance is an alkyl, cycloalkyl, aryl, aralkyl, substituted alkyl, substituted aryl, or substituted aralkyl having from 1 to about 20 carbon atoms. Examples of alkoxy or aryloxy groups (—OR) groups include, but are not limited to, methoxy, ethoxy, propoxy, butoxy, phenoxy, substituted phenoxy, and the like.

In each instance, sulfur groups are sulfur-containing groups, examples of which include, but are not limited to, —SR and the like, including substituted derivatives thereof, wherein R in each instance is an alkyl, cycloalkyl, aryl, aralkyl, substituted alkyl, substituted aryl, or substituted aralkyl having from 1 to about 20 carbon atoms.

In each instance, nitrogen groups are nitrogen-containing groups, which include, but are not limited to, $-NH_2$, —NHR, $-NR_2$, and the like, including substituted derivatives thereof, wherein R in each instance is an alkyl, cycloalkyl, aryl, aralkyl, substituted alkyl, substituted aryl, or substituted aralkyl having from 1 to about 20 carbon atoms.

In each instance, phosphorus groups are phosphorus-containing groups, which include, but are not limited to, $-PH_2$, —PHR, $-PR_2$, $P(OR)_2$, and the like, including substituted derivatives thereof, wherein R in each instance is an alkyl, cycloalkyl, aryl, aralkyl, substituted alkyl, substituted aryl, or substituted aralkyl having from 1 to about 20 carbon atoms.

In each instance, arsenic groups are arsenic-containing groups, which include, but are not limited to, —AsHR, $-AsR_2$, $-As(OR)_2$, and the like, including substituted derivatives thereof, wherein R in each instance is an alkyl, cycloalkyl, aryl, aralkyl, substituted alkyl, substituted aryl, or substituted aralkyl having from 1 to about 20 carbon atoms.

In each instance, carbon groups are carbon-containing groups, which include, but are not limited to, alkyl halide groups that comprise halide-substituted alkyl groups with 1 to about 20 carbon atoms, aralkyl groups with 1 to about 20 carbon atoms, cyano, and the like, including substituted derivatives thereof, having from 1 to about 20 carbon atoms.

In each instance, silicon groups are silicon-containing groups, which include, but are not limited to, silyl groups such alkylsilyl groups, arylsilyl groups, arylalkylsilyl groups, siloxy groups, and the like, which in each instance have from 1 to about 20 carbon atoms. For example, silicon groups include trimethylsilyl and phenyloctylsilyl groups.

In each instance, germanium groups are germanium-containing groups, which include, but are not limited to, germyl groups such as alkylgermyl groups, arylgermyl groups, arylalkylgermyl groups, germyloxy groups, and the like, which in each instance have from 1 to about 20 carbon atoms.

In each instance, tin groups are tin-containing groups, which include, but are not limited to, stannyl groups such as alkylstannyl groups, arylstannyl groups, arylalkylstannyl groups, stannoxy (or "stannyloxy") groups, and the like, which in each instance have from 1 to about 20 carbon atoms. Thus, tin groups include, but are not limited to, stannoxy groups.

In each instance, lead groups are lead-containing groups, which include, but are not limited to, alkyllead groups, aryllead groups, arylalkyllead groups, and the like, which in each instance, have from 1 to about 20 carbon atoms.

In each instance, boron groups are boron-containing groups, which include, but are not limited to, $-BR_2$, $-BX_2$, —BRX, wherein X is a monoanionic group such as halide, hydride, alkoxide, alkyl thiolate, and the like, and wherein R in each instance is an alkyl, cycloalkyl, aryl, aralkyl, substituted alkyl, substituted aryl, or substituted aralkyl having from 1 to about 20 carbon atoms.

In each instance, aluminum groups are aluminum-containing groups, which include, but are not limited to, $-AlR_2$, $-AlX_2$, —AlRX, wherein X is a monoanionic group such as halide, hydride, alkoxide, alkyl thiolate, and the like, and wherein R in each instance is an alkyl, cycloalkyl, aryl, aralkyl, substituted alkyl, substituted aryl, or substituted aralkyl having from 1 to about 20 carbon atoms.

Examples of organometallic groups that may be used as substituents in each instance, include, but are not limited to, organoboron groups, organoaluminum groups, organogallium groups, organosilicon groups, organogermanium groups, organotin groups, organolead groups, organo-transition metal groups, and the like, having from 1 to about 20 carbon atoms.

In another aspect of this invention, any substituent on the substituted aryl group of $R^1$, any substituent on the substituted hydrocarbyl group of $R^2$, and any substituent on the substituted hydrocarbyl group of $R^3$ can be independently selected from a variety of chemical moieties including, but not limited to, those disclosed herein, also including, but not limited to, heteroatom-substituted analogs of these moieties, as long as these groups do not terminate the synthetic method for fulvene synthesis. The term heteroatom-substituted analogs will be well-known to one of ordinary skill, and include, but are not limited to, chemical moieties that include such heteroatoms as boron, aluminum, gallium, indium, silicon, germanium, tin, lead, nitrogen, phosphorus, arsenic, antimony, oxygen, sulfur, selenium, tellurium, and the like.

Preparation of Bis(cyclopentadienyl)methanes and Related Compounds

The present invention also encompasses a method of synthesizing compounds comprising cyclopentadienyl-type moieties that are linked by a $>CR^1(CH_2R^2)$ group, namely bis(cyclopentadienyl)methane compounds, and various analogs thereof such as (cyclopentadienyl)(indenyl)methane and (cyclopentadienyl)(fluorenyl)methane compounds. Thus, in a further aspect, this invention provides a method of making a compound having the formula $C_4R^3_4CHCR^1(CH_2R^2)(QH)$ and the structure:

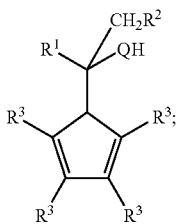

comprising:
1) contacting in a nonprotic solvent:
   a) a ketone of the formula $O=CR^1CH_2R^2$; and
   b) a cyclopentadienyl compound comprising $Mg(C_5R^3_4H)X$, $Mg(C_5R^3_4H)_2$, or a combination thereof; followed by
   c) a proton source;
to form a compound having the formula $C_4R^3_4C=CR^1CH_2R^2$ and the structure:

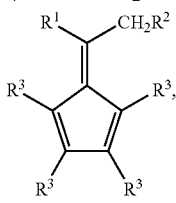

or an isomer thereof,
wherein:
   $R^1$ is an aryl or substituted aryl group having up to about 20 carbon atoms;
   $R^2$ is a hydrocarbyl or substituted hydrocarbyl group having from 1 to about 20 carbon atoms, or hydrogen;
   $R^3$, in each instance, is independently selected from a hydrocarbyl or substituted hydrocarbyl group having from 1 to about 20 carbon atoms, or hydrogen; and
   X is Cl, Br, or I; and
2) contacting
   a) $C_4R^3_4C=CR^1CH_2R^2$ with MQ, wherein M is Li, Na, K, MgX, or $Mg_{0.5}$, wherein X is Cl, Br, or I, and wherein Q is a cyclopentadienyl, an indenyl, a fluorenyl, or a substituted analog thereof; followed by
   b) a proton source, to form $C_4R^3_4CHCR^1(CH_2R^2)(QH)$.

In another aspect, this method can further comprise isolating the compound $C_4R^3_4CHCR^1(CH_2R^2)(QH)$.

The possible selections for $R^1$, $CH_2R^2$, $R^3$, the ketone, the cyclopentadienyl compound, the molar ratio of $Mg(C_5H_5)X$ to ketone, the nonprotic solvent, the substituents, and the like, are the same as those disclosed herein for the method to prepare the fulvene.

In the compound $C_4R^3_4CHCR^1(CH_2R^2)(QH)$, the substituent Q can be cyclopentadienyl or substituted cyclopentadienyl having up to about 20 carbon atoms. In addition, Q can be indenyl or substituted indenyl having up to about 20 carbon atoms. Further, Q can be fluorenyl or substituted fluorenyl having up to about 20 carbon atoms. The possible substituents on the substituted aryl group of $R^1$, any substituent on the substituted hydrocarbyl group of $R^2$, any substituent on the substituted hydrocarbyl group of $R^3$, any substituent on the substituted cyclopentadienyl, any substituent on the substituted indenyl, and any substituent on the substituted fluorenyl are also disclosed herein.

Preparation of Metallocene Complexes

Numerous processes to prepare and use metallocene-based catalyst that can be employed in this invention have been reported. For example, U.S. Pat. Nos. 4,939,217, 5,191,132, 5,210,352, 5,347,026, 5,399,636, 5,401,817, 5,420,320, 5,436,305, 5,451,649, 5,496,781, 5,498,581, 5,541,272, 5,554,795, 5,563,284, 5,565,592, 5,571,880, 5,594,078, 5,631,203, 5,631,335, 5,654,454, 5,668,230, 5,705,579, 6,187,880, 6,509,427, and 6,524,987 describe such methods, each of which is incorporated by reference herein, in its entirety. Other processes to prepare metallocene compounds that can be employed in this invention have been reported in references such as: Köppl, A. Alt, H. G. *J. Mol. Catal A.* 2001, 165, 23; Kajigaeshi, S.; Kadowaki, T.; Nishida, A.; Fujisaki, S. *The Chemical Society of Japan*, 1986, 59, 97; Alt, H. G.; Jung, M.; Kehr, G. *J. Organomet. Chem.* 1998, 562, 153-181; and Alt, H. G.; Jung, M. *J. Organomet. Chem.* 1998, 568, 87-112; each of which is incorporated by reference herein, in its entirety.

Further, additional processes to prepare metallocene compounds that can be employed in this invention have been reported in: *Journal of Organometallic Chemistry*, 1996, 522, 39-54, which is incorporated by reference herein, in its entirety. The following treatises also describe such methods: Wailes, P. C.; Coutts, R. S. P.; Weigold, H. in Organometallic Chemistry of Titanium, Zirconium, and Hafnium, Academic; New York, 1974; Cardin, D. J.; Lappert, M. F.; and Raston, C. L.; Chemistry of Organo-Zirconium and -Hafnium Compounds; Halstead Press; New York, 1986; each of which is incorporated by reference herein, in its entirety.

In one aspect, this invention provides a method of making an ansa-metallocene having the formula $(\eta^5-C_5R^3_4)CR^1(CH_2R^2)(\eta^5-Q)M^1X_2$, wherein $M^1$ is titanium, zirconium, or hafnium, and X is a halide, comprising:

1) contacting in a nonprotic solvent:
   a) a ketone of the formula $O=CR^1CH_2R^2$; and
   b) a cyclopentadienyl compound comprising $Mg(C_5R^3_4H)X$, $Mg(C_5R^3_4H)_2$, or a combination thereof; followed by
   c) a proton source;
to form a compound having the formula $C_4R^3_4C=CR^1CH_2R^2$ and the structure:

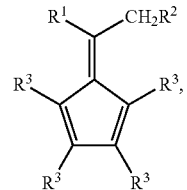

wherein:
   $R^1$ is an aryl or substituted aryl group having up to about 20 carbon atoms;
   $R^2$ is a hydrocarbyl or substituted hydrocarbyl group having from 1 to about 20 carbon atoms, or hydrogen;
   $R^3$, in each instance, is independently selected from a hydrocarbyl or substituted hydrocarbyl group having from 1 to about 20 carbon atoms, or hydrogen; and
   X is Cl, Br, or I;
2) contacting
   a) $C_4R^3_4C=CR^1CH_2R^2$ with MQ, wherein M is Li, Na, K, MgX, or $Mg_{0.5}$, and X is Cl, Br, or I; and wherein Q is a cyclopentadienyl, an indenyl, a fluorenyl, or a substituted analog thereof; followed by b) a proton source, to form $C_4R^3{}_4CHCR^1(CH_2R^2)(QH)$ having the structure:

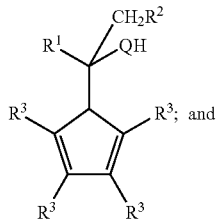

3) contacting $C_4R^3{}_4CHCR^1(CH_2R^2)(QH)$ with about 2 equivalents of a base and a compound of the formula $M^1X_4$.

In a further aspect, this method further comprises isolating $(\eta^5\text{-}C_5R^3{}_4)CR^1(CH_2R^2)\text{-}(\eta^5\text{-}Q)M^1X_2$.

The possible selections for $R^1$, $CH_2R^2$, $R^3$, the ketone, the cyclopentadienyl compound, the molar ratio of $Mg(C_5H_5)X$ to ketone, the nonprotic solvent, the substituents, and the like, are the same as those disclosed herein for the method to prepare the fulvene.

In another aspect, concerning the method to prepare a compound of the formula $(\eta^5\text{-}C_5R^3{}_4)CR^1(CH_2R^2)(\eta^5\text{-}Q)M^1X_2$, the substituent Q can be cyclopentadienyl or substituted cyclopentadienyl having up to about 20 carbon atoms. In addition, Q can be indenyl or substituted indenyl having up to about 20 carbon atoms. Further, Q can be fluorenyl or substituted fluorenyl having up to about 20 carbon atoms. The possible substituents on the substituted aryl group of $R^1$, any substituent on the substituted hydrocarbyl group of $R^2$, any substituent on the substituted hydrocarbyl group of $R^3$, any substituent on the substituted cyclopentadienyl, any substituent on the substituted indenyl, and any substituent on the substituted fluorenyl are also disclosed herein.

In a further aspect, the ansa-metallocene can comprise compound I with the following formula:

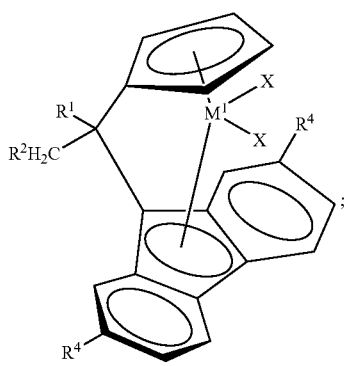

wherein $M^1$ is Ti, Zr, or Hf; $R^1$ is an aryl or substituted aryl group having up to about 20 carbon atoms; $CH_2R^2$ is an alkenyl or alkyl group having from about 3 to about 12 carbon atoms; and $R^4$ is H or a hydrocarbyl group having from 1 to about 12 carbon atoms.

In still another aspect, the ansa-metallocene can comprise compound II with the following formula:

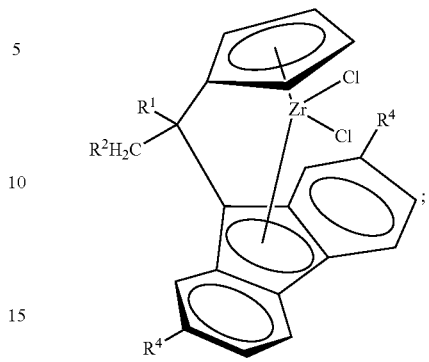

wherein $R^1$ is phenyl; $CH_2R^2$ is 3-butenyl ($CH_2CH_2CH=CH_2$), 4-pentenyl ($CH_2CH_2CH_2CH=CH_2$), 5-hexenyl ($CH_2CH_2CH_2CH_2CH=CH_2$), 6-heptenyl ($CH_2CH_2CH_2CH_2CH_2CH=CH_2$), 7-octenyl ($CH_2CH_2CH_2CH_2CH_2CH_2CH=CH_2$), 3-methyl-3-butenyl ($CH_2CH_2C(CH_3)=CH_2$), 4-methyl-3-pentenyl ($CH_2CH_2CH=C(CH_3)_2$), or a substituted analog thereof having up to about 12 carbon atoms; and $R^4$ is H or t-butyl.

EXAMPLES

The present invention is further illustrated by the following examples, which are not to be construed in any way as imposing limitations upon the scope thereof. On the contrary, it is to be clearly understood that resort may be had to various other aspects, features, embodiments, modifications, and equivalents thereof which, after reading the description herein, may suggest themselves to one of ordinary skill in the art without departing from the spirit of the present invention or the scope of the appended claims.

General Details

The solvents used in the following Examples were dried and distilled using standard methods.

Pentenylphenone (1-phenyl-5-hexen-1-one) was prepared by a procedure analogous to that described by Köppl and Alt for butenylphenone (1-phenyl-4-penten-1-one) in *Journal of Molecular Catalysis A: Chemical*, 2001, 165, 23, which is incorporated by reference herein in its entirety, but using 4-bromo-1-butene in the place of allylbromide. This preparation is shown schematically in Step 1 and Step 2 of Scheme 1 in *Journal of Molecular Catalysis A: Chemical*, 2001, 165, 23.

Cyclopentadienyl magnesium chloride (CpMgCl) was purchased from Boulder Scientific as solution in THF. CpMgCl can also be prepared according to the procedure detailed in U.S. Pat. No. 6,175,027, which is incorporated herein by reference in its entirety. U.S. Pat. No. 6,175,027 also provides a general description of cyclopentadienyl Grignard synthesis methods. A method for preparing CpMgX was also reported by Stille and Grubbs in *J. Org. Chem.*, (1989), 54, 441, which is incorporated herein by reference in its entirety.

Dicyclopentadienyl magnesium could be prepared according to Duff, Hitchcock, Lappert, and Taylor, *J. Organometal. Chem.* (1985), 293, 271, which is incorporated herein by reference in its entirety.

The Gas Chromatographic (GC) analysis data illustrating carbinol formation reported in Table 1, in which retention times are recorded, were performed as follows. Data were recorded on an HP 5890 GC using a 30 m crosslinked methylsiloxane column, 0.32 mm ID, 0.25 micron stationary phase. Analysis conditions are as follows. Set-up was 44 psi hydrogen pressure, 50 psi air pressure, 44 psi helium pressure and a splitless flow. The injector temperature was set at 300° C. and the detector was set at 310° C. For the GC run, the initial temperature of 40° C. was held for 1 minute, followed by a ramp of 20° C./minute to a final temperature of 300° C. The final temperature was held for 15 minutes.

The Nuclear Magnetic Resonance (NMR) spectra reported herein were obtained on a Varian Mercury Plus 300 NMR spectrometer operating at 300 MHz for $^1$H NMR (CDCl$_3$ solvent, referenced against the peak of residual CHCl$_3$ at 7.24 ppm) and 75 MHz for $^{13}$C NMR (CDCl$_3$ solvent, referenced against central line of CHCl$_3$ at 77.00 ppm).

Example 1

Preparation of 6-phenyl-6-(3-butenyl)fulvene using Cyclopentadienyl Grignard Reagents Method 1. A 1 L round bottomed flask was charged with 1-phenyl-4-penten-1-one (50 g, 313 mmol), THF (270 mL), and a stir bar, and cooled to 0° C. Cyclopentadienyl magnesium chloride (325 mL of an approximately 1.1M solution in THF, 345 mmol) was added dropwise via an addition funnel, while maintaining the temperature at 0° C. The resulting mixture was slowly warmed to room temperature, refluxed for 3 hours, and then cooled to room temperature. This reaction mixture was then neutralized with 2M HCl, and extracted with pentane. The pentane extracts were dried with sodium sulfate, filtered, and the filtrate evaporated to dryness to afford 70 g of red oil. Elution of this oil through silica using heptane afforded 39 g (60% isolated and purified yield) of the product 6-phenyl-6-(3-butenyl)fulvene as a red oil.

Method 2. An alternative preparation of 6-phenyl-6-(3-butenyl)fulvene to that detailed in Method 1 is to allow the reaction to proceed at room temperature for about 4 days, prior to neutralizing the reaction mixture with HCl. Following a similar workup as that detailed in Method 1, at least about an 80% conversion to the desired product 6-phenyl-6-(3-butenyl)fulvene was obtained, with 100% of this product constituting the desired isomer (100% selectivity).

Method 3. A 1 L round bottomed flask was charged with 1-phenyl-4-penten-1-one (49.1 g, 307 mmol), THF (200 mL), and a stir bar, and cooled in an ice bath. Cyclopentadienyl magnesium chloride (330 mL of approximately 1 M solution in THF, 330 mmol) was added dropwise over 1 hour. The pale red solution was stirred overnight while warming to room temperature. The solution was then refluxed for 4.5 hours, during which time the red color intensified. After being stirred overnight at room temperature again, the solution was acidified by first adding 5.5 g of ammonium chloride in 100 mL of water, and then adding 50 mL of 1 M HCl. The product was extracted with pentane, and the pentane extracts were collected, washed with water, and dried over sodium sulfate. Elution through silica with heptane and concentration under vacuum afforded 38.6 g (55% isolated and purified yield) of the product 6-phenyl-6-(3-butenyl)fulvene as a red oil.

Example 2

Comparative Preparation of 6-phenyl-6-(3-butenyl)fulvene using Lithium Cyclopentadienyl A 1 L round bottomed flask was charged with 1-phenyl-4-penten-1-one (38.4 g, 240 mmol), THF (100 mL), and a stir bar, and cooled to −78° C. Cyclopentadienyl lithium (245 mmol) in THF (200 mL) was added dropwise via an addition funnel while maintaining the temperature at −78° C. The resulting mixture was slowly warmed to room temperature and stirred for 3 days. After this time, the reaction mixture was neutralized with 2M HCl and extracted with pentane. The pentane extracts were collected and dried with sodium sulfate, filtered, and the filtrate evaporated to dryness to afford 46 g of red oil. Elution of this oil through silica using heptane afforded 19 g (38%) of the product 6-phenyl-6-(3-butenyl)fulvene as a red oil.

Example 3

Comparative Preparation of 6-phenyl-6-(3-butenyl)fulvene using KOEt/EtOH

A solution of potassium ethoxide (5.30 g, 63 mmol) dissolved in 250 mL of absolute ethanol was prepared. This KOEt/EtOH solution was cooled in a dry ice bath and 10 mL of freshly cracked cyclopentadiene was added. The solution was stirred for 3 hours at dry ice temperature, after which time 10 μL (62.4 mmol) of 1-phenyl-4-penten-1-one was added. This solution was stirred for 4 hours at dry ice temperature, then warmed to 5° C. and stirred for 65 hours. While the reaction mixture was then cooled to ice temperature, 50 mL of 3 M HCl, followed by 100 mL of water were added. The product was extracted from the reaction solution with both ether and pentane, and the combined organic layers were washed with water. The resulting solution was dried over sodium sulfate, filtered, and concentrated to afford 12.65 g of the crude product as a red oil. The desired fulvene, 6-phenyl-6-butenylfulvene, was shown by GC to comprise 77.6% of the red oil, but the undesired isomeric product constituted 15.3% of the oil. The crude oil was chromatographed through silica using hexane to elute the fractions, a process that made it possible to lower the isomeric product to less than about 4% of the material. The combined fractions of fulvene obtained in this way weighed 3.32 g (17%).

Example 4

Comparative Preparation of 6-phenyl-6-(3-butenyl)fulvene using NaOEt/EtOH

A flask was charged with 1-phenyl-4-penten-1-one (45 g of 94% pure, 264 mmol) and cooled to 0° C. under nitrogen. Sodium ethoxide (100 mL of 21 wt. % in ethanol, 268 mmol) was added via an addition funnel followed by addition of freshly cracked cyclopentadiene (43 mL, 528 mmol) via syringe. This reaction was warmed to room temperature and stirred for 4 hours. An aliquot of the reaction mixture was analyzed by GC, which indicated that all of the ketone had been consumed. Water was added to quench the reaction followed by extraction of the product with pentane. The pentane extract was dried over magnesium sulfate, filtered, and the filtrate was evaporated to dryness under reduced pressure to afford a red oil (51.5 g). The desired fulvene was shown by GC to comprise 82% of the product, but the isomeric product constituted 16% of the resulting product.

Example 5

Comparative Preparation of 6-phenyl-6-(3-butenyl)fulvene using Lithium Cyclopentadienyl Butyl lithium in hexanes, 59 mL (94.4 mmol), was added to 8.0 mL of freshly cracked cyclopentadiene dissolved in 100 mL of THF and cooled in a dry ice bath. After the addition was complete, the dry ice bath was removed and the reaction mixture was stirred for 3.5 hours yielding a white slurry. This slurry was cooled in an ice bath and 15.1 g of 1-phenyl-4- penten-1-one (94.2 mmol) as a solution in 40 mL of THF was added. The ice bath was then removed and the resulting yellow solution was stirred for 18 hours. An aliquot of the reaction solution was analyzed by GC and the ketone-to-product molar ratio was 78:17. After the reaction mixture was stirred for 20 more minutes, the molar ratio was 74:20. Refluxing this reaction mixture for 24 hours gave a ratio of 50:31. Subsequent stirring of the reaction mixture for 5 days at room temperature provided a ratio to 40:37. The reaction was abandoned.

Example 6

Comparative Preparation of
6-phenyl-6-(3-butenyl)fulvene using Lithium
Cyclopentadienyl A flask was charged with solid lithium cyclopentadienide (1 g, 13.9 mmol), diethyl ether (25 mL), and 1-phenyl-4-penten-1-one (2 g, 12.5 mmol) in succession. This reaction mixture was stirred at room temperature, and aliquots from the reaction were periodically analyzed by GC over the course of six days. After six days the ketone-to-product ratio was 88:12. The reaction was abandoned

Example 7

Comparative Preparation of
6-phenyl-6-(3-butenyl)fulvene using NaOMe/MeOH

A flask was charged with sodium methoxide (54 mg, 1 mmol), methanol (20 mL), freshly cracked cyclopentadiene (0.08 mL), and 1-phenyl-4-penten-1-one (160 mg, 1 mmol) in succession. This reaction mixture was stirred at room temperature for 24 hours. An aliquot was analyzed by GC and the ketone-to-product ratio was 56:44 and the isomeric ratio of the desired fulvene product to undesired fulvene product was 3:1. The reaction was abandoned.

Example 8

Comparative Preparations of
6-phenyl-6-(3-butenyl)fulvene using
Cyclopentadiene and Pyrollidine in MeOH A flask was charged with 1-phenyl-4-penten-1-one (2 g, 12.5 mmol) and methanol (20 mL) and was cooled to 0° C. Freshly cracked cyclopentadiene (2.0 mL) and pyrollidine (2.3 mL) were then added in succession via syringe. The reaction was warmed to room temperature and stirred for 24 hours. An aliquot of the reaction was analyzed by GC and the ketone-to-product ratio was 85:15, while the isomeric ratio of the desired fulvene product to the undesired fulvene product was 13:1. The reaction was abandoned.

Example 9

Preparation of 6-phenyl-6-(4-pentenyl)fulvene using
Cyclopentadienyl Grignard Reagents A 1 L round bottomed flask was charged with 1-phenyl-5-hexene-1-one (see: Köppl and Alt *Journal of Molecular Catalysis A: Chemical*, 2001, 165, 23) (50 g, 287 mmol), THF (100 mL), and a stir bar, and cooled to 0° C. Cyclopentadienyl magnesium chloride (325 mL of an approximately 1.1 M solution in THF, 345 mmol) was added dropwise via an addition funnel while maintaining the temperature at 0° C. The resulting mixture was slowly warmed to room temperature, then refluxed for 3 hours, and subsequently cooled to room temperature. The reaction was neutralized with 2M HCl, and extracted with pentane. The pentane extracts were dried with sodium sulfate, filtered, and evaporated to dryness affording 67 g of red oil. Elution of this oil through silica using heptane afforded 33 g (52%) of 6-phenyl-6-(4-pentenyl)fulvene as a red oil. $^1$H NMR (CDCl$_3$, 30° C.): δ 7.38 (m, 5H, C$_6$H$_5$), 6.63 (m, 1H), 6.58 (m, 1H), 6.49 (m, 1H), 6.11 (m, 1H, fulvene CH), 5.75 (m, 1H, alkenyl CH), 4.97 (m, 2H, alkenyl CH$_2$), 2.94 (t, 2H), 2.07 (dd, 2H, CH$_2$), 1.53 (t, 2H, CH$_3$).

Example 10

Preparation of
1-cyclopentadiene-1-phenylpent-4-ene-1-ol using
Grignard Reagents The present invention also provides a method to prepare the corresponding carbinol intermediates, resulting from nucleophilic addition of the cyclo-pentadienyl-type reagents to the aryl alkyl ketones or aryl alkenyl ketones followed by hydrolysis, as follows.

A sample of 1-phenylpent-4-ene-1-one 50 mL, 49.7 grams, 310 mmoles) was dissolved in 200 mL of dry THF under nitrogen and the flask was cooled in an ice bath. While this solution was stirred vigorously, 350 mL of 1.07 M CpMgCl (375 mmoles; Mg:ketone ratio of 1.2:1) was added over a period of 60 minutes. The resulting yellow solution was stirred for 20 hours at room temperature, over which time it developed a red color. A small aliquot of this reaction solution was then removed and hydrolyzed, followed by a gas chromatography analysis (GC) using a flame ionization detector. The major peaks identified by this GC detection were as shown in Table 1.

TABLE 1

Gas Chromatographic[1] Analysis Data Illustrating Carbinol Formation

| Retention Time(min) | Percent | Identification |
|---|---|---|
| A. Reaction for 20 hours at Room Temperature | | |
| 4.16 | 16 | Dicyclopentadiene |
| 6.56 | 3.8 | Ketone |
| 8.91 | 32 | Fulvene |
| 9-10 (broad) | >25% | Carbinol |
| B. Reaction for 44 hours at Room Temperature, Followed by 3.5 Hours Reflux | | |
| 4.16 | 8.6 | Dicyclopentadiene |
| 6.56 | 14.6 | Ketone |
| 8.91 | 66.9 | Fulvene |
| 9-10 (broad) | <2 | Carbinol |

[1]Conditions for obtaining retention times in the GC analysis reported in this Table are described in the General Details section.

Stirring the reaction mixture for an additional day (24 hours) at room temperature produced no further changes in the GC of an aliquot. The reaction solution was then refluxed for 3.5 hours. A subsequent GC analysis of an aliquot of this reaction solution which was then hydrolyzed revealed that much of the carbinol had been converted to the fulvene, as shown in Table 1. However, it was also observed that the amount of ketone increased during this process. Since the absolute amount of dicyclopentadiene would not have decreased during this process, and while not intending to be bound by theory, it is believed that this increase in the ketone amount is likely due to the decomposition of some of the carbinol back to the starting material. Again, while not intending to be bound by theory, this observation suggests an explanation for why excess CpMgCl works well during the fulvene preparation. Further, the conversion of carbinol to fulvene shown in section B of Table 1 suggests why elevated temperatures, including but not limited to reflux, are useful to convert the carbinol to the fulvene without isolating the carbinol first.

Example 11

Preparation of 1-(phenyl)-1-(4-pentenyl)-1-(cyclopentadienyl)-1-(fluorenyl)-methane A 1 L round bottomed flask was charged with fluorene (23.2 g, 139.6 mmol), THF (400 mL), and a stir bar, and cooled to −78° C. as n-butyl lithium (165 mmol) was slowly added. The mixture was warmed to room temperature, stirred overnight, then cooled to 0° C., and 6-phenyl-6-(4-pentenyl) fulvene (38 g, 171 mmol), dissolved in 400 mL of THF was added via cannula. After the resulting mixture was stirred for two days at room temperature, the reaction was quenched with saturated $NH_4Cl$ solution, the organic material extracted with diethyl ether, and the ether extracts dried over anhydrous $Na_2SO_4$. Upon solvent removal, 69.1 g of a yellow oil was isolated. Chromatography of this oil through silica using heptane afforded 31.7 g (58%) of the desired ligand, 1-(phenyl)-1-(4-pentenyl)-1-(cyclopentadienyl)-1-(fluorenyl)methane, that was used without further purification.

Example 12

Preparation of 1-($\eta^5$-cyclopentadienyl)-1-($\eta^5$-9-fluorenyl)-1-phenylhex-5-ene Zirconium Dichloride A round bottomed flask was charged with the ligand 1-(phenyl)-1-(4-pentenyl)-1-(cyclopentadienyl)-1-(fluorenyl)methane, (7.20 g, 18.6 mmol), diethyl ether (250 mL), stir bar, and cooled to −78° C. as n-butyl lithium (40 mmol) was slowly added. The mixture was warmed to room temperature, stirred overnight, and then added via cannula to $ZrCl_4$ (4.3 g, 18.5 mmol) which was being stirred in pentane (250 mL) at 0° C. The resulting orange mixture was warmed to room temperature, stirred overnight, centrifuged, and the supernatant was decanted. The remaining solid was extracted with methylene chloride. This methylene chloride extract was centrifuged, and the supernatant was decanted and subsequently evacuated to dryness affording the product as a reddish solid (7.1 g, 70%). $^1$H NMR ($CDCl_3$, 30° C.): δ 8.19 (m, 2H), 7.87 (m, 2H), 7.63 (m, 3H), 7.48 (m, 4H), 6.94 (t, 1H), 6.21 (d, 1H, ArCH), 6.47 (m, 1H), 6.34 (m, 1H), 5.95 (m, 1H), 5.78 (m, 1H, CpH), 5.84 (m, 1H pentenyl-CH), 5.09 (m, 2H, pentenyl-$CH_2$), 2.96 (m, 2H), 2.22 (m, 2H), 1.63 (m, 2H). $^{13}$C NMR ($CDCl_3$, 30° C.): δ 142.77, 138.19, 129.99, 129.88, 128.82, 128.67, 127.81, 127.57, 127.26, 125.35, 125.29, 125.23, 124.55, 124.07, 123.87, 123.83, 123.42, 122.77, 121.29, 120.23, 117.88, 115.57, 112.49, 103.62, 103.20, 79.10, 54.04, 39.98, 33.85, 23.38.

Although any methods, devices, and materials similar to or equivalent to those described herein can be used in the practice or testing of the invention, the typical methods, devices and materials are herein described.

All publications and patents mentioned herein are incorporated herein by reference in their entireties, for the purpose of describing and disclosing, for example, the constructs and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

To the extent that any definition or usage provided by any document incorporated herein by reference conflicts with the definition or usage provided herein, the definition or usage provided herein controls.

For any particular compound disclosed herein, any general structure presented also encompasses all conformational isomers, regioisomers, and stereoisomers that may arise from a particular set of substituents. The general structure also encompasses all enantiomers, diastereomers, and other optical isomers whether in enantiomeric or racemic forms, as well as mixtures of stereoisomers, as the context requires.

We claim:

1. A method of making a compound, the method comprising:
   contacting in a nonprotic solvent:
   a ketone having a formula of $O=CR^1CH_2R^2$; and
   a cyclopentadienyl compound comprising $Mg(C_5R^3{}_4H)X$; followed by
   a proton source;
   to form a compound having a formula of $C_4R^3{}_4C=CR^1CH_2R^2$ and a structure:

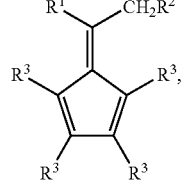

or an isomer thereof; wherein
   $R^1$ is an aryl or substituted aryl group having up to about 20 carbon atoms;
   $R^2$ is a hydrocarbyl or substituted hydrocarbyl group having from 1 to about 20 carbon atoms, or hydrogen;
   $R^3$, in each instance, is independently selected from a hydrocarbyl or substituted hydrocarbyl group having from 1 to about 20 carbon atoms, or hydrogen; and
   X is Cl, Br, or I.

2. The method of claim 1, wherein any substituent on the substituted aryl group of $R^1$, any substituent on the substituted hydrocarbyl group of $R^2$, and any substituent on the substituted hydrocarbyl group of $R^3$ are independently selected from an aliphatic group, an aromatic group, a cyclic group, a combination of aliphatic and cyclic groups, an oxygen group, a sulfur group, a nitrogen group, a phosphorus group, an arsenic group, a carbon group, a silicon group, a germanium group, a tin group, a lead group, a boron group, an aluminum group, an inorganic group, an organometallic group, or a substituted derivative thereof, any one of which having from 1 to about 20 carbon atoms; a halide; or hydrogen.

3. The method of claim 1, wherein $R^1$ is phenyl, naphthyl, or a substituted analog thereof having up to about 20 carbon atoms.

4. The method of claim 1, wherein $R^2$ is an alkyl, aryl, alkenyl, or a substituted analog thereof, having from 1 to about 20 carbon atoms, or hydrogen.

5. The method of claim 1, wherein $R^2$ is an alkyl group or an alkenyl group having from 3 to about 10 carbon atoms.

6. The method of claim 1, wherein $CH_2R^2$ is:
   $CH_2CH_3$;
   $CH_2CH_2CH_3$;
   $CH_2CH_2CH_2CH_3$;
   $CH_2CH_2CH_2CH_2CH_3$;
   $CH_2CH_2CH_2CH_2CH_2CH_3$;
   $CH_2CH_2CH_2CH_2CH_2CH_2CH_3$;
   $CH_2CH_2CH_2CH_2CH_2CH_2CH_2CH_3$;
   $CH_2CH_2CH_2CH_2CH_2CH_2CH_2CH_2CH_3$;
   $CH_2CH_2CH_2CH_2CH_2CH_2CH_2CH_2CH_2CH_3$;
   $CH_2CH=CH_2$;
   $CH_2CH_2CH=CH_2$;
   $CH_2CH_2CH_2CH=CH_2$;
   $CH_2CH_2CH_2CH_2CH=CH_2$;
   $CH_2CH_2CH_2CH_2CH_2CH=CH_2$;
   $CH_2CH_2CH_2CH_2CH_2CH_2CH=CH_2$;
   $CH_2CH_2CH_2CH_2CH_2CH_2CH_2CH=CH_2$;
   $CH_2CH_2CH_2CH_2CH_2CH_2CH_2CH_2CH=CH_2$;
   $CH_2CH_2C(CH_3)=CH_2$;

CH$_2$CH$_2$CH=C(CH$_3$)$_2$;
CH$_2$C$_6$H$_5$;
CH$_2$C$_6$H$_4$Me;
CH$_2$C$_6$H$_3$Me$_2$;
CH$_2$C$_6$H$_2$Me$_3$;
CH$_2$C$_6$H$_4$(C$_6$H$_{11}$);
CH$_2$C$_6$H$_4$(C$_6$H$_5$);
CH$_2$C$_6$H$_4$(C$_4$H$_9$); or
a substituted analog thereof having up to about 20 carbon atoms.

7. The method of claim 1, wherein R$^3$, in each instance, is independently selected from an alkyl group or an alkenyl group having from 1 to about 20 carbon atoms; or hydrogen.

8. The method of claim 1, wherein R$^3$, in each instance, is independently selected from an alkyl group or an alkenyl group having from 1 to about 12 carbon atoms; or hydrogen.

9. The method of claim 1, wherein R$^3$, in each instance, is hydrogen.

10. The method of claim 1, wherein the ketone is:
O=C(C$_6$H$_5$)CH$_2$CH=CH$_2$;
O=C(C$_6$H$_5$)CH$_2$CH$_2$CH=CH$_2$;
O=C(C$_6$H$_5$)CH$_2$CH$_2$CH$_2$CH=CH$_2$;
O=C(C$_6$H$_5$)CH$_2$CH$_2$CH$_2$CH$_2$CH=CH$_2$;
O=C(C$_6$H$_5$)CH$_2$CH$_2$CH$_2$CH$_2$CH$_2$CH=CH$_2$;
O=C(C$_6$H$_4$CH$_3$)CH$_2$CH=CH$_2$;
O=C(C$_6$H$_4$CH$_3$)CH$_2$CH$_2$CH=CH$_2$;
O=C(C$_6$H$_4$CH$_3$)CH$_2$CH$_2$CH$_2$CH=CH$_2$;
O=C(C$_6$H$_4$CH$_3$)CH$_2$CH$_2$CH$_2$CH$_2$CH=CH$_2$;
O=C(C$_6$H$_4$CH$_3$)CH$_2$CH$_2$CH$_2$CH$_2$CH$_2$CH=CH$_2$;
O=C[C$_6$H$_3$(CH$_3$)$_2$]CH$_2$CH=CH$_2$;
O=C[C$_6$H$_3$(CH$_3$)$_2$]CH$_2$CH$_2$CH=CH$_2$;
O=C[C$_6$H$_3$(CH$_3$)$_2$]CH$_2$CH$_2$CH$_2$CH=CH$_2$;
O=C[C$_6$H$_3$(CH$_3$)$_2$]CH$_2$CH$_2$CH$_2$CH$_2$CH=CH$_2$;
O=C[C$_6$H$_3$(CH$_3$)$_2$]CH$_2$CH$_2$CH$_2$CH$_2$CH$_2$CH=CH$_2$;
O=C[C$_6$H$_2$(CH$_3$)$_3$]CH$_2$CH=CH$_2$;
O=C[C$_6$H$_2$(CH$_3$)$_3$]CH$_2$CH$_2$CH=CH$_2$;
O=C[C$_6$H$_2$(CH$_3$)$_3$]CH$_2$CH$_2$CH$_2$CH=CH$_2$;
O=C[C$_6$H$_2$(CH$_3$)$_3$]CH$_2$CH$_2$CH$_2$CH$_2$CH=CH$_2$;
O=C[C$_6$H$_2$(CH$_3$)$_3$]CH$_2$CH$_2$CH$_2$CH$_2$CH$_2$CH=CH$_2$;
O=C[C$_6$H$_4$(C$_6$H$_{11}$)]CH$_2$CH=CH$_2$;
O=C[C$_6$H$_4$(C$_6$H$_{11}$)]CH$_2$CH$_2$CH=CH$_2$;
O=C[C$_6$H$_4$(C$_6$H$_{11}$)]CH$_2$CH$_2$CH$_2$CH=CH$_2$;
O=C[C$_6$H$_4$(C$_6$H$_{11}$)]CH$_2$CH$_2$CH$_2$CH$_2$CH=CH$_2$;
O=C[C$_6$H$_4$(C$_6$H$_{11}$)]CH$_2$CH$_2$CH$_2$CH$_2$CH$_2$CH=CH$_2$;
O=C[CH$_2$C$_6$H$_4$(C$_6$H$_5$)]CH$_2$CH=CH$_2$;
O=C[CH$_2$C$_6$H$_4$(C$_6$H$_5$)]CH$_2$CH$_2$CH=CH$_2$;
O=C[CH$_2$C$_6$H$_4$(C$_6$H$_5$)]CH$_2$CH$_2$CH$_2$CH=CH$_2$;
O=C[CH$_2$C$_6$H$_4$(C$_6$H$_5$)]CH$_2$CH$_2$CH$_2$CH$_2$CH=CH$_2$;
O=C[CH$_2$C$_6$H$_4$(C$_6$H$_5$)]CH$_2$CH$_2$CH$_2$CH$_2$CH$_2$CH=CH$_2$;
O=C[CH$_2$C$_6$H$_4$(C$_4$H$_9$)]CH$_2$CH=CH$_2$;
O=C[CH$_2$C$_6$H$_4$(C$_4$H$_9$)]CH$_2$CH$_2$CH=CH$_2$;
O=C[CH$_2$C$_6$H$_4$(C$_4$H$_9$)]CH$_2$CH$_2$CH$_2$CH=CH$_2$;
O=C[CH$_2$C$_6$H$_4$(C$_4$H$_9$)]CH$_2$CH$_2$CH$_2$CH$_2$CH=CH$_2$,
O=C[CH$_2$C$_6$H$_4$(C$_4$H$_9$)]CH$_2$CH$_2$CH$_2$CH$_2$CH$_2$CH=CH$_2$;
O=C(naphthyl)CH$_2$CH=CH$_2$;
O=C(naphthyl)CH$_2$CH$_2$CH=CH$_2$;
O=C(naphthyl)CH$_2$CH$_2$CH$_2$CH=CH$_2$;
O=C(naphthyl)CH$_2$CH$_2$CH$_2$CH$_2$CH=CH$_2$;
O=C(naphthyl)CH$_2$CH$_2$CH$_2$CH$_2$CH$_2$CH=CH$_2$; or any analog thereof wherein the alkenyl group is saturated; or any isomer thereof.

11. The method of claim 1, wherein the ketone is:
O=C(C$_6$H$_5$-p-alkyl)CH$_2$CH$_2$CH=CH$_2$,
O=C(C$_6$H$_5$-p-alkyl)CH$_2$CH$_2$CH$_2$CH=CH$_2$,
O=C(C$_6$H$_5$-p-cycloalkyl)CH$_2$CH$_2$CH=CH$_2$, or
O=C(C$_6$H$_5$-p-cycloalkyl)CH$_2$CH$_2$CH$_2$CH=CH$_2$;
wherein p-alkyl and p-cycloalkyl have up to about 12 carbon atoms.

12. The method of claim 1, wherein the cyclopentadienyl compound comprises Mg(C$_5$H$_5$)X, wherein X is Cl or Br, and the molar ratio of Mg(C$_5$H$_5$)X to ketone is greater than about 1.

13. The method of claim 1, wherein the cyclopentadienyl compound comprises Mg(C$_5$H$_5$)X, wherein X is Cl or Br, and the molar ratio of Mg(C$_5$H$_5$)X to ketone is greater than about 1.2.

14. The method of claim 1, wherein the cyclopentadienyl compound comprises Mg(C$_5$H$_5$)X, wherein X is Cl or Br, and the molar ratio of Mg(C$_5$H$_5$)X to ketone is greater than about 1.5.

15. The method of claim 1, wherein the nonprotic solvent is an ether having from 2 to about 20 carbon atoms, THF, a substituted analog thereof, or any combination thereof.

16. The method of claim 1, wherein the nonprotic solvent is dimethyl ether, diethyl ether, diisopropyl ether, di-n-propyl ether, di-n-butyl ether, methyl t-butyl ether, diphenyl ether, THF, 1,2-dimethoxyethane, or any combination thereof.

17. The method of claim 1, wherein the nonprotic solvent comprises THF.

18. The method of claim 1, wherein the nonprotic solvent comprises THF, and contacting occurs at a temperature greater than about 40° C. for at least about 10 hours.

19. The method of claim 1, wherein the nonprotic solvent comprises THF, and contacting occurs at a temperature greater than about 50° C. for a time from about 5 to about 10 hours.

20. The method of claim 1, wherein the nonprotic solvent comprises THF, and contacting occurs at a temperature greater than about 65° C. for a time from about 1 to about 2 hours.

21. The method of claim 1, wherein the nonprotic solvent comprises an ether with a boiling point greater than about 40° C., and contacting occurs at a temperature greater than about 40° C. for at least about 5 hours.

22. The method of claim 1, wherein contacting occurs at a temperature greater than about 40° C. for at least about 5 hours at a pressure such that the boiling point of the nonprotic solvent is about equal to or greater than the contacting temperature.

23. A method of making a compound comprising:
contacting in a nonprotic solvent:
a ketone having a formula of O=CR$^1$CH$_2$R$^2$; and
a cyclopentadienyl compound comprising Mg(C$_5$R$^3$$_4$H)X; followed by
a proton source;
to form a first compound having a formula of C$^4$R$^3$$_4$C=CR$_1$CH$_2$R$^2$ and a structure:

or an isomer thereof,
wherein:
R$^1$ is an aryl or substituted aryl group having up to about 20 carbon atoms;
R$^2$ is a hydrocarbyl or substituted hydrocarbyl group having from 1 to about 20 carbon atoms, or hydrogen;
R$^3$, in each instance, is independently selected from a hydrocarbyl or substituted hydrocarbyl group having from 1 to about 20 carbon atoms, or hydrogen; and
X is Cl, Br, or I; and contacting
the first compound with MQ, wherein M is Li, Na, K, MgX, or Mg$_{0.5}$, wherein X is Cl, Br, or I, and wherein Q is a cyclopentadienyl, an indenyl, a fluorenyl, or a substituted analog thereof; followed by
a proton source, to form a second compound having a formula of C$_4$R$^3_4$CHCR$^1$(CH$_2$R$^2$)(QH) and a structure:

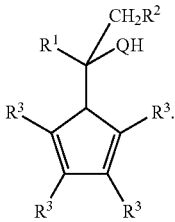

24. The method of claim 23, comprising isolating the second compound.

25. The method of claim 23, wherein Q is cyclopentadienyl or substituted cyclopentadienyl having up to about 20 carbon atoms.

26. The method of claim 23, wherein Q is indenyl or substituted indenyl having up to about 20 carbon atoms.

27. The method of claim 23, wherein Q is fluorenyl or substituted fluorenyl having up to about 20 carbon atoms.

28. A method of making an ansa-metallocene comprising:
contacting in a nonprotic solvent:
a ketone having a formula of O=CR$^1$CH$_2$R$^2$; and
a cyclopentadienyl compound comprising Mg(C$_5$R$^3_4$H)X; followed by
a proton source;
to form a first compound having a formula of C$_4$R$^3_4$C=CR$^1$CH$_2$R$^2$ and a structure:

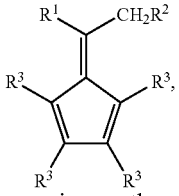

or an isomer thereof,
wherein:
R$^1$ is an aryl or substituted aryl group having up to about 20 carbon atoms;
R$^2$ is a hydrocarbyl or substituted hydrocarbyl group having from 1 to about 20 carbon atoms, or hydrogen;
R$^3$, in each instance, is independently selected from a hydrocarbyl or substituted hydrocarbyl group having from 1 to about 20 carbon atoms, or hydrogen; and
X is Cl, Br, or I;
contacting
the first compound with MQ, wherein M is Li, Na, K, MgX, or Mg$_{0.5}$, wherein X is Cl, Br, or I, and wherein Q is a cyclopentadienyl, an indenyl, a fluorenyl, or a substituted analog thereof; followed by
a proton source, to form a second compound having a formula of C$_4$R$^3_4$CHCR$^1$CH$_2$R$^2$)(QH) and a structure:

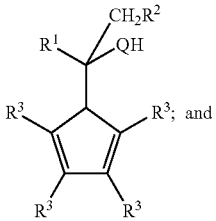

contacting the second compound with about 2 equivalents of a base and a compound having a formula of M$^{1X}_4$ to form the ansa-metallocene having a general formula of ($\eta^5$-C$_5$R$^3_4$)CR$^1$(CH$_2$R$^2$)($\eta^{5-Q)M1}$)X$_2$, wherein M$^1$ is titanium, zirconium, or hafnium, and X is a halide.

29. The method of claim 28, comprising isolating the ansa-metallocene.

30. The method of claim 28, wherein Q is cyclopentadienyl or substituted cyclopentadienyl having up to about 20 carbon atoms.

31. The method of claim 28, wherein Q is indenyl or substituted indenyl having up to about 20 carbon atoms.

32. The method of claim 28, wherein Q is fluorenyl or substituted fluorenyl having up to about 20 carbon atoms.

33. The method of claim 28, wherein the ansa-metallocene comprises compound I with the following formula:

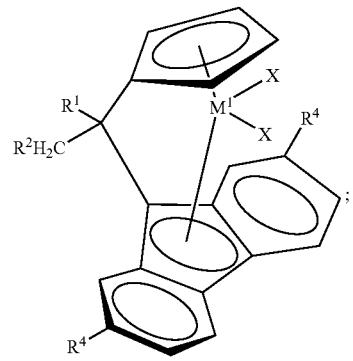

wherein M$^1$ is Ti, Zr, or Hf; R$^1$ is an aryl or substituted aryl group having up to about 20 carbon atoms; CH$_2$R$^2$ is an alkenyl or alkyl group having from about 3 to about 12 carbon atoms; and R$^4$ is H or a hydrocarbyl group having from 1 to about 12 carbon atoms.

34. The method of claim 28, wherein the ansa-metallocene comprises compound II with the following formula:

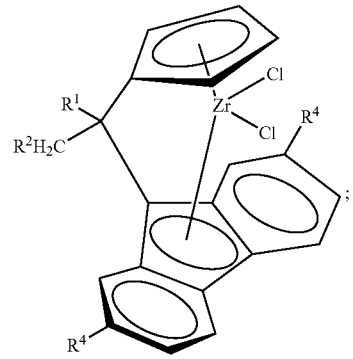

wherein R$^1$ is phenyl; CH$_2$R$^2$ is 3-butenyl (CH$_2$CH$_2$CH=CH$_2$), 4-pentenyl (CH$_2$CH$_2$CH$_2$CH=CH$_2$), 5-hexenyl (CH$_2$CH$_2$CH$_2$CH$_2$CH=CH$_2$), 6-heptenyl (CH$_2$CH$_2$CH$_2$CH$_2$CH$_2$CH=CH$_2$), 7-octenyl (CH$_2$CH$_2$CH$_2$CH$_2$CH$_2$CH$_2$CH=CH$_2$),3-methyl-3-butenyl (CH$_2$CH$_2$C(CH$_3$)=CH$_2$), 4-methyl-3-pentenyl (CH$_2$CH$_2$CH=C(CH$_3$)$_2$), or a substituted analog thereof having up to about 12 carbon atoms; and R$^1$ is H or t-butyl.

* * * * *